United States Patent [19]

Maurer

[11] Patent Number: 4,680,309

[45] Date of Patent: Jul. 14, 1987

[54] METHODS AND COMPOSITIONS FOR TREATING INFLAMMATION OR ARTHRITIS

[75] Inventor: Gerald L. Maurer, Fairfield, Ohio

[73] Assignee: National Research Laboratories, Cincinnati, Ohio

[21] Appl. No.: 825,674

[22] Filed: Feb. 3, 1986

Related U.S. Application Data

[63] Continuation of Ser. No. 447,424, Dec. 6, 1982, abandoned.

[51] Int. Cl.$^4$ ............... A01N 55/02; A61K 31/30
[52] U.S. Cl. ............... 514/499; 556/114; 514/492; 514/494; 514/495; 514/496; 514/500; 514/501; 514/503; 514/505
[58] Field of Search ............... 514/499

[56] References Cited

U.S. PATENT DOCUMENTS

| | | | |
|---|---|---|---|
| 4,055,655 | 10/1977 | Maurer et al. | 424/294 |
| 4,129,509 | 12/1978 | Shringarpurey et al. | |
| 4,180,473 | 12/1979 | Maurer et al. | 424/294 X |
| 4,221,785 | 9/1980 | Sorenson | 424/230 |
| 4,278,610 | 7/1981 | Maurer et al. | 260/429 R X |
| 4,287,190 | 9/1981 | Boettcher et al. | 424/230 |
| 4,373,953 | 2/1983 | Deinet et al. | 424/294 X |

OTHER PUBLICATIONS

Sorenson, J of Medicinal Chem., V. 19, No. 1, pp. 135–148 (1976).
Sorenson, Inflammation, 1976, vol. 1, No. 3, pp. 317–331.
Chemical Abstracts, 84, 38591r (1976).
Chemical Abstracts 85, 116777t (1976).
Katz, Rheumatic Diseases Diagnosis and Management, J. B. Lippincott Co., Phila., Toronto, pp. 27–29 (1977).
Whitehouse, M. W. and Walter, W. R.: The Copper Bracelet for Arthritis, Med. J. Australia, (1):938, (Jun. 18, 1977).
Sorenson, J. R. J.: Development of Copper Complexes for Potential Therapeutic Use, Agents and Actions, vol. 8 Supplement, pp. 305–325, 360–367 (1981).
Lengfelder, E. and Elstner, E. F. (Munich): Determination of the Superoxide Dismutating Activity of D-Penicillamine Copper, Hoppe-Seyler's Z. Physiol. Chem. 359:751–757 (Jun. 1978).
Chou, W. S., Savage, J. E. and O'Dell, B. L. (Columbia, M. O.): Relation of Monoamine Oxidase Activity and Collagen Cross-Linking in Copper-Deficient and Controlled Tissues, Proc. Soc. Exp. Biol. Med. 128:948–952 (Aug.–Sep., 1968).
Scudder, P., Stocks, J. and Dormandy, T. L. (London): The Relationship Between Erythrocyte Superoxide Dismutase and Erythrocyte Copper Levels in Normal Subjects and in Patients with Rheumatoid Arthritis, Clin. Chim. Acta. 69:397–403 (Jun. 15, 1976).
Younes, M. and Weser, U. (Tubingen): Reactivity of Superoxide Dismutase-Active Cu(II) Complexes on the Rate of Adrenochrome Formation, Febs. Lett. 71:87–90 (Nov. 15, 1976).
Joester, K.-E., Jun, G., Weber, U. and Weser, U. (Tubingen): Superoxide Dismutase Activity of $Cu^{2+}$-Amino Acid Chelates, Febs. Lett. 25:25–28, (Sep. 1, 1972).
Lin, P. S., Kwock, L. and Goodchild, N. T. (Boston): Copper Superoxide Radical Diethyldithiocarbamate, and Bleomycin Cytotoxicity (Letter to Edition): Lancet 1:777 (Apr. 7, 1979).
Oberley, J. W., Oberley, T. D. and Buttner, G. R. (Iowa City): Cell Differentiation, Aging in Cancer: The Possible Roles of Superoxide in Superoxide Dismutases. Med. Hypoth: 6:249–268 (Mar. 1980).
Somville, M. and Remacle, J. (Namur): Superoxide Dismutases in Aging Fibroblasts, Arch. Int. Physiol. Biochim. 88:B99–B100 (May, 1980).

(List continued on next page.)

Primary Examiner—Helen M. S. Sneed
Attorney, Agent, or Firm—Wood, Herron & Evans

[57] ABSTRACT

A method of treating inflammation or arthritis with metal complexes that can traverse skin and animal cell membranes intact and effectively deliver and release metal ions in a controlled manner upon demand at the targeted inflammatory or arthritic areas containing endogenous reacting moieties which demand the metal ions. The metal complexes have an aqueous proton induced dissociation property represented by a sigmoidally-shaped curve on a cartesian coordinate plot of the negative log of the metal ion concentration versus the negative log of hydrogen ion concentration. This dissociation property enables the metal complexes to release metal ions in a controlled manner upon demand at the targeted inflammatory or arthritic areas containing endogenous reacting moieties which demand the metal ions. The metal complexes can be effectively administered either topically or subcutaneously. Upon topical application, the metal complexes are dispersed in a vehicle to provide a buffered composition to neutralize the initial acidic layer of the skin. These unique and advantageous properties permit the metal complexes to be incorporated into vehicles with an adjusted pH minimizing premature release of the metal ions prior to reaching the targeted inflammatory or arthritic areas. Further, the metal complexes can be dispersed in a greaseless cold cream vehicle formulated to avoid or minimize undesirable chemical incompatibilities. An example of a topical composition employed is disodium-monocopper(II) citrate in an amount of about 10% w/w in a water-dispersible cream base vehicle comprising an oil-in-water emulsion having a pH of about 7.0.

38 Claims, No Drawings

OTHER PUBLICATIONS

Menander-Huber, K. B. and Huber, W. (Mountainview, Calif.): Orgotein, The Drug Version of Bovine Cu-Zn Superoxide Dismutase II. A Summary Account of Clinical Trials in Man and Animals, In: Michaelson, A. N., McCord, J. M. and Friodivich, I. (Eds): Superoxide Dismutases, London: Academic Press, pp. 537–549, (1977).

Gerber, D. A. (New York): Increased Copper Ligand Reactivity in the Urine of Patients with Rheumatoid Arthritis, Arthritis Rheum. 9:795–803 (Dec. 1966).

Sorenson, J. R. J.: The Anti-Inflammatory Activities of Copper Complexes, In: Helmut, S. (Ed.): Metal Ions in Biological Systems, vol. 14, Chp. 4, New York: Marcel Dekker, Inc., pp. 77–124, (1982).

Useful Formulas, In: Martin, E. W. et al (Eds.): Remington's Practice of Pharmacy, 12th Edition, Chp. 99, Easton: Mack Publishing Company, pp. 1802–1803, (1961).

Sorenson, J. R. J.: Therapeutic Uses of Copper, In: Nrigu, J. O. (Ed.): Copper in the Enviroment, Part II, Chp. 5, John Wiley & Sons, Inc., pp. 104–162 (1979).

Walker, W. R. et al.: Anti-Inflammatory Activity of a Dermally Applied Copper Salicylate Preparation (Alcusal ®), Agents and Actons, 10:38–47 (1980).

Walker, W. R. and Reeves, R. R.: Perfusion of Intact Skin by a Saline Solution of Bis-(Blycinato) Copper (II), Bioinorganic Chem. 7:271–276 (1977).

Walker, W. R. and Daphne, M. K.: An Investigation of the Therapeutic Value of the 'Copper Bracelet' Dermal Assimilation of Copper in Arthritic/Rheumatoid Condition, Agents and Actions, 6(4):454–459 (1976).

Somville, M. and Remacle, J.: Superoxide Dismutases in Ageing Human Fibroblasts, Societe Bedge de Biochimie, pp. B99–B100 (Dec. 15, 1979).

Dollwet, H. H. A. et al.: Anti-Inflammatory Properties of Copper Implants in the Rat Paw Edema: A Preliminary Study, Agents and Actions, 11:746–749 (1981).

Jackson, G. E. et al.: Metal-Ligand Complexes Involved in Rheumatoid Arthritis-VI, J. Inorg. Nucl. Chem. 40:1227–1234 (1978).

Giuseppe, A. et al: Metal-Ligand Complexes Involved in Rheumatoid Arthritis-V, J. Inorg. Nucl. Chem. 40:1221–1226 (1978).

Beveridge, S. J. et al.: Anti-Inflammatory Activity of Copper Salicylates Applied to Rats Percutaneously in Dimethyl Sulphexide with Glycerol, J. Pharm. Pharmacol. 32:452–427 (1980).

METHODS AND COMPOSITIONS FOR TREATING INFLAMMATION OR ARTHRITIS

This application is a continuation of application Ser. No. 447,424, filed Dec. 6, 1982, now abandoned.

BACKGROUND OF THE INVENTION

Inflammation is a local and protective response to tissure injury and destruction of cells. The precise elements constituting the inflammatory response vary according to the site of injury, the state of the body, and the injurious agent, such as bacteria or trauma. Should the inflammatory response become impaired or compromised, however, the corresponding tissue will undergo a degenerative process stimulating further injury and cell destruction. Obviously, then, the inflammatory response embodies a multifaceted process that is required to promote and rehabilitate normal tissue function. Therefore, since the inflammatory response is generally similar with various stimuli, it can be viewed and treated as a relatively nonspecific response.

Inflammation may be manifested in numerous ways and one of the more well-known forms is arthritis. By definition, arthritis constitutes inflammation of a joint. Unfortunately, approximately 14% of the present United States population suffers from some type of arthritic manifestations. Further, if arthritis is ineffectively treated, it can develop into an extremely painful, degenerative and crippling disease. The present anti-arthritic therapy constitutes painful, toxic, inconvenient and ineffective protocols designed primarily to alleviate the symptoms rather than the causes. Thus, in light of current knowledge and the notorious effects of arthritis, there obviously is a critical need to develop an effective, safe, painless and convenient form of treatment that can be employed to alleviate successfully the causes of arthritic inflammation.

Today, methods of treating inflammation or arthritis with metals such as copper are well established. For instance, it has been known since ancient Egypt that copper has been indicated for therapeutically treating granulomatous inflammation. In a another instance, it has been established that the dissolution of copper from copper jewelry, for example, bracelets, worn in contact with skin appears to have therapeutic anti-inflammatory effects. Whitehouse, M. W. and Walter, W. R.: The Copper Bracelet for Arthritis. *Med. J. Australia.* (1):938 June 18, 1977. In still another instance, subdermal copper implants in rats have been demonstrated to exhibit anti-inflammatory activity. In a further instance, a neutral copper (II) bis(glycine) complex perfused through cat skin demonstrating that skin is permeable to soluble copper. In still a further instance several oral and parenteral copper complexes have been somewhat successfully used in the treatment of inflammation or arthritis. Such examples include penicillamine, Cu(II)salicylate, $Cu(II)_2(aspirinate)_4$ and $Cu(II)_2(acetate)_4$. Sorenson, J. R. J.: Development of Copper Complexes for Potential Therapeutic Use. *Agents and Actions.* Vol. 8 Supplement, pp. 305 at 307-310, 1981. Finally, dermally applied copper complexes have been confirmed as pharmacoactive anti-inflammatory agents. Walker et al: Dermal Copper Drugs: A Copper Bracelet and Cu(II) Salicylate Complexes. *Agents and Actions.* Vol. 8 Supplement pp. 359-367, 1981. Unfortunately, the current copper-containing dosage forms have been somewhat ineffective as a means to maximize delivery of copper to the strategic inflammatory or arthritic sites.

As with most other therapeutics, the precise mechanism of activity and, indeed the pertinence of copper per se to therapeutic use in inflammatory or arthritic conditions are somewhat hypothetical. However, there have been suggested in the literature several plausible biochemical mechanisms of action that are responsible for the anti-inflammatory or antiarthritic activity exhibited by copper complexes, and those are incorporated herein. Sorenson, J. R. J.: Development of Copper Complexes for Potential Therapeutic Use. *Agents and Actions.* Vol. 8 Supplement, pp. 305, at 313, 1981. With respect to the importance of copper as a therapeutic agent in arthritic conditions, there is an abundancy of significant evidence. For example, penicillamine, an oral potent copper complexing agent, exhibits effective anti-inflammatory action in arthritis. Lengfelder, E. and Elstner, E. F. (Munich): Determination of the Superoxide Dismutating Activity of D-penicillamine Copper. *Hoppe-Seyler's Z. Physiol. Chem.* 59:751-757, June 1978. Collagen and elastin cross linkages are poorly formed, if at all, in copper deficiency resulting in weakened tissues. Chou, W. S., Savage, J. E. and O'Dell, B. L. (Columbia, MO): Relation of Monoamine Oxidase Activity and Collagen Crosslinking in Copper-deficient and Control Tissues. *Proc. Soc. Exp. Biol. Med.* 128:948-952, August-September 1968. Reduced superoxide dismutase (SOD), a copper dependent enzyme, in the leukocytes of patients with rheumatoid arthritis leads to the induction of degenerative changes. Scudder, P., Stocks, J. and Dormandy, T. L. (London): The Relationship between Erythrocyte Superoxide Dismutase and Erythrocyte Copper Levels in Normal Subjects and in Patients with Rheumatoid Arthritis. *Clin. Chim Acta* 69:397-403, June 15, 1976. Various chelates have demonstrated superoxide dismutasic activity including copper penicillamine, copper salicylate, copper acetylsalicylate and copper-para- aminosalicylate. Younes, M. and Weser, U. (Tübingen): Reactivity of Superoxide Dismutase-active Cu(II) Complexes on the Rate of Adrenochrome Formation. *FEBS Lett.* 71:87-90, Nov. 15, 1976. Copper amino acid compounds exhibit similar activities; e.g., copper tyrosine and copper lysine. Joester, K.-E., Jung, G., Weber, U. and Weser, U. (Tubingen): Superoxide Dismutase Activity of $Cu^{2+}$-amino Acid Chelates. *FEBS Lett.* 25:25-28, Sept. 1, 1972. On the other hand, diethyldithiocarbamate, a very potent copper chelant, inhibits superoxide dismutase in cell cultures, presumably by leaching the SOD copper. The SOD activity is restored by replacing the copper. Lin, P. S., Kwock, L. and Goodchild, N. T. (Boston): Copper Superoxide Radical, Diethyldithiocarbamate, and Bleomycin Cytotoxicity (Letter to editor): *Lancet* 1:777, Apr. 7, 1979. In human fibroblasts there is a production of free radical oxygen which is accompanied by a parallel rise in the concentration of cytoplasmic superoxide dismutase and correlates in the deterioration and aging of cell populations. Oberley, J. W., Oberley, T. D. and Buettner, G. R. (Iowa City): Cell Differentiation, Aging and Cancer: The Possible Roles of Superoxide and Superoxide Dismutases. *Med. Hypoth.* 6:249-268, March 1980; Somville, M. and Remacle, J. (Namur): Superoxide Dismutases in Aging Fibroblasts. *Arch. Int. Physiol. Biochim.* 88:B99-B100, May 1980. Orgotein, a copper-zinc protein which exhibits superoxide dismutase activity, has been used therapeutically in patients with rheumatoid arthritis and has been found to be as effective as gold or penicillamine. Menander-Huber, K. B. and Huber, W. (Mountain View, CA): Orgotein, the Drug Version of Bovine Cu-Zn Superoxide Dismutase. II. A Summary Account of Clinical Trials in Man and Animals. In: Michelson, A. M., McCord, J. M. and Fridovich, I. (Eds): *Superoxide and Superoxide Dismutases*. London:Academic Press, 1977. pp. 537-549. Further, the formation of Cu-cuprizone complex is prevented in the urine of 80% of rheumatoid arthritis patients and in only 5% of the "normal" population. Gerber, D. A. (New York): Increased Copper Ligand Reactivity in the Urine of Patients with Rheumatoid Arthritis. *Arthritis Rheum.* 9:795-803, December 1966. Finally, it has been observed that copper containing components in the blood increase in patients with rheumatoid arthritis and other degenerative diseases. This evidence patently demonstrates that copper is pharmacoactive and plays a key role in maintaining as well as repairing tissues to facilitate remission of inflammatory diseases. Thus, the prior art, as a whole, verifies that copper in the blood is vital as a "putative modulator" of inflammation. Sorenson, J. R. J.: Development of Copper Complexes for Potential Therapeutic Use. *Agents and Actions.* Vol. 8 Supplement, pp. 305-325, 1981.

Presently, conventional anti-inflammatory therapy includes application of heat, exercise, salicylates to tolerance, indomethacin or butazolidin, and oral and intra-articular steroids. The above anti-inflammatory protocol, however, is less than optimum because it provides only a means to inhibit some component of the inflammatory process in a generally temporary or transient fashion. In other words, it treats the symptoms rather than promoting tissue repair or alleviating the causes of the degeneration. Sorenson, J. R. J.: The Anti-Inflammatory Activities of Copper Complexes. Metal Ions in Biological Systems. IN: Helmut, S. (Ed): *Inorganic Drugs in Deficiency and Disease.* Vol. 14 New York: Marcel Dekker, Inc. p. 78 (1982).

In other instances of anti-inflammatory therapy, various prior art approaches have been taken to employ copper as a means to directly alleviate the causes of inflammation and to promote tissue repair. These have led to several improved copper compositions and dosage forms in an effort to maximize delivery of copper to the inflammatory areas. Representative of prior art literature in this area are Sorenson, J. R. J.: Development of Copper Complexes for Potential Therapeutic Use. *Agents and Actions.* Vol. 8 Supplement, pp. 305-325, (1981). Such literature and efforts of others in substance have been directed to overcoming the present ineffective and inconvenient treatment of inflammation or arthritis with copper. In substance, in such prior art processes, there are apparently four dosage forms made available that incorporate copper. Such dosage forms include parenteral (subcutaneous, intravascular, or intramuscular injection), oral, topical or inserts. The parenteral copper dosage forms are obviously painful, inconvenient, require the presence of a physician, and cause further irritation at the site of injection. The oral dosage forms, on the other hand, are poorly absorbed by the gastric lining, reducing their anti-inflammatory activity. There are several factors known, however, that can be attributed to their poor absorption upon oral ingestion. In one instance, gastric acidity contributes to the possible destruction of the oral copper-containing complexes. In another instance, the use of ionic suspending agents, e.g., tragacanth and acacia, can either sequester the copper ions from these complexes or form quaternary complexes. Finally, single oral doses are poorly absorbed probably for the reasons stated above. With respect to the copper inserts, they too are painful, require a physician to be inserted, and can be intentionally or accidentally removed. Finally, the topical copper dosage forms are commonly used when selecting a route in medicating inflammation or arthritis, as disclosed above. The administration of such topical dosage forms are patently desirable because of their unique and advantageous characteristics. Notwithstanding the notoriety for topical dosage forms, the past and present topical copper complexes have not performed to their anticipated expectations as a means to effectively and conveniently treat inflammation or arthritis with copper. For example, the application of metal salts to proteinaceous membranes, such as skin, results in the attachment of the copper ions to the membrane components to form copper proteinates or salts. Thus, little if any copper ion, in the soluble, ionized state is ever introduced into the targeted inflammatory or athritic areas. Further, copper salts can be corrosive to the skin possibly causing the patient to incur various types of lytic reactions. To overcome this undesirable characteristic, copper ions are complexed with a ligand or chelant to form a metal complex. In other words, the copper is shielded from binding to the membrane components. An example of such topical complexes include copper-amine complexes and copper EDTA. Unfortunately, there are undesirable characteristics associated with these complexes which obviate their usefulness. For example, these highly stable copper complexes are capable of traversing the membranes, but because the copper ions are so very tightly bound to the complex and/or shielded from the copper acceptor sites, the copper ions are essentially unavailable to perform any useful therapeutic function. Moreover, when salicylates are used as the ligands additional problems can be incurred, particularly if used in patients or animals with allergies to salicylates. Regarding topical treatment with copper jewelry, copper absorption is dependent upon dissolution of copper from the jewelry by the bearer's sweat. Thus, predetermined therapeutic amounts of copper cannot be reliably delivered to the targeted inflammatory or arthritic areas. Further, an undesirable green ring or mark is often left on the bearer's skin that is associated with copper jewelry use.

It is apparent from the above brief overview of the importance of copper to inflammation or arthritis and the current state of knowledge that there are critical needs that must be met and problems to be solved, so that inflammation or arthritis may be more effectively and conveniently treated.

SUMMARY OF THE INVENTION

The invention is directed to a method for treating inflammation or arthritis by transporting metal ions in controlled amounts to the targeted inflammatory or arthritic areas. A particular class of metal complexes has been found especially suited to first deliver and then effectively release metal ions to prevent or reduce the inflammatory processes. Broadly, the method comprises the application of an effective amount of a 1:1 metal complex of a multivalent heavy metal ion bound to a polyfunctional organic ligand. In one preferred form to assist in the application of the metal complex, it is dispersed in a suitable vehicle. The 1:1 metal complex has an aqueous proton induced dissociation property represented by a sigmoidally-shaped curve on a cartesian coordinate plot of the negative log of the metal ion concentration versus the negative log of the hydrogen ion concentration. It has been found that metal complexes having such a dissociation property provide a means to transport copper, for instance, into the body and then enable its controlled release at the targeted inflammatory or arthritic sites.

Thus, this invention fulfills a need in treating inflammation or arthritis where the intact transport of metal ions to the inflammatory or arthritic areas is required for controlled release of metal ion amounts upon demand. This is particularly illustrated in the topical anti-inflammatory or anti-arthritic application of this invention where metal ions are required to be introduced through the skin into the inflammatory or arthritic areas in large amounts. The skin is slightly acidic, i.e., about pH 4.5 to 6.5 and the tissue, blood or stratum below the skin is closer to a pH of 7. According to this invention, copper complexes are delivered through the skin intact for release of copper ions at the pathological pH of about 7 below the skin. The method of this invention provides release of large amounts of metal ion from the metal complexes at a pH of about 7, because of their relative instabilities at about pH 7 or the pathological pH below the skin. These preferred metal complexes are very stable, even at high alkaline pHs, and relatively inert to organic moieties. Yet, upon demand, by reason of the unique dissociation property as demonstrated by sigmoidally shaped behavior on a pM-pH diagram, these agents offer controlled release of metal ions at a pH wherein inflammation or arthritis is believed to occur. Such method of transport employing a complex which dissociates upon demand at the pH most amenable to the activity of the moiety being acted upon, for example, the endogenous biochemical complexes that require copper for their activation to promote anti-inflammatory or anti-arthritic responses, is a unique, advantageous and novel method to treat said diseases and causes of said diseases.

The metal transport method of this invention is, thus, to be differentiated from methods which employ other complexing agents and other means for transporting metal ions. For example, the complexes of this invention are to be differentiated from other metal complexes wherein metal cations have been complexed with organic ligands represented by ethylenediaminetetraacetic acid (EDTA), diethylenetriaminepentaacetic acid (DTPA), other amino acids, or the like which have relatively high stability or chemical inertness. Further, the complexes of this invention are to be differentiated from other metal complexes wherein the metal cations have been complexed with organic ligands such as salicylic or acetylsalicylic acid, which possess pharmacologic activity, but are either so stable or ionic in nature that they are relatively ineffective. Known metal complexes simply do not deliver a controlled and effective amount of a metal ion to an inflammatory disease. Rather, known metal complexes by reason of their stability will tend to dissociate to a lesser extent in rather linear fashions over the normal physiological pH range. Furthermore, this invention provides an anti-inflammatory or anti-arthritic metal complex which has a dual character, i.e., aqueous solubility in high concentration by reason of its ionic character and a stability of the complexed metal. This property of solubility in water or neutral, acid, or alkaline media enables the production of concentrates capable of producing upon demand metal ions in the physiological range of about 4 to about 9, especially about 7. Such a solubility property is to be distinguished from the rather insoluble metal compounds of the prior art which employed metal cation-anionic components which are virtually insoluble in aqueous media; or those metal complexes which, even though they are soluble, bind the metal ion in such a complexed state that it is only slightly dissociated and, therefore, scarcely available for anti-inflammatory or antiarthritic action. Also, metal complexes employed in the methods of this invention release large amounts of metal ion from their coordinate structures most preferably at a pH of about 7 or less, i.e., where inflammatory or arthritic conditions are encountered. Upon demand, by reason of their unique dissociation property as demonstrated by sigmoidally shaped behavior on a pM-pH diagram, these anti-inflammatory or anti-arthritic agents offer controlled release of metal ions at a pH compatible with inflammatory or arthritic conditions.

Additionally, the metal complexes of this invention can be dispersed and buffered in a suitable vehicle to assist in their applications. The methods of this invention comprise topical or parenteral administration which includes topical application to the area of the skin where the inflammatory or arthritic disorder is believed to exist. In such vehicles, the neutralizing acidity of the skin has been overcome so that the complexes will effectively release metal ions upon demand at the site of inflammation.

It is acknowledged by the inventor herein that his U.S. Pat. Nos. 4,055,655, 4,129,509, and 4,180,473 disclose the metal complexes which have now been found especially effective against inflammatory processes according to the present invention. However, even though such complexes were reported as effective antimicrobial agents and metal transport agents, it had not been previously known that they may be uniquely effective against the dreaded inflammatory processes such as arthritis. Furthermore, such findings and other advantages of the present invention as described herein are considered unexpected and unobvious.

DETAILED DESCRIPTION OF INVENTION

In a presently preferred form, the anti-inflammatory or anti-arthritic agent of this invention comprises a monometal complex of multivalent heavy metal and a polyfunctional organic ligand in a ratio of 1:1 of the metal to the ligand, the complex having a dissociation property represented by a sigmoidally shaped plot on a pM-pH diagram. Specific examples of the metal complex are dialkali metal monocopper(II) citrates represented by disodium-, dipotassium- or dilithium-monocopper(II) citrate. These dialkali monocopper(II) citrates have a dissociation property represented by a sigmoidal plot, wherein the curve of two directions meet at a point within the pH range of about 7 to about 9. It has been established that these monocopper(II) complexes in basic media, on the order of about pH 9 to about 12, are very stable, i.e., have an effective stability constant, $K_{eff}$, of the order of about $10^{12}$ to about $10^{13}$. However, $K_{eff}$ of these monocopper(II) citrate complexes at a pH of about 7-9 are on the order of about $10^5$ to about $10^{12}$. Therefore, at a pH of around 7, the effective stability constant of the monocopper(II) citrate complex is considerably lower (a thousand to a several hundreds of thousand times lower) and a significant free $Cu^{++}$ concentration is available for anti-inflammatory and anti-arthritic activity. For example, about 10% of the copper in the complex is in the ionized state at or about pH 7 while approximately 0.1% of the copper is ionized at or about pH 9.

Thus, it is to be understood that the anti-inflammatory or anti-arthritic complexes of this invention are sensitive to pH, and as the pH is lowered to or below about 7, then copper ion is made more available. If tissue is intact, i.e., healthy without trauma, then there are few, if any, free endogenous reacting moieties to induce the dissociation of copper ions. If there is trauma caused by inflammation, then the copper ions are induced to dissociate and complex with the endogenous reacting moieties associated with such trauma, thereby reducing or alleviating the inflammation. In general, the complexes will then tend to dissociate over a pH range of about 3 to about 12. Above about pH 12, the complexes tend to be destroyed by the alkaline media, precipitating from the media as hydrous metal oxides. Below about pH 7, the instability of the metal complex results in high concentrations of the free $Cu^{++}$ upon demand, as explained to effect antiinflammatory or anti-arthritic activities. At the pathological pH of about 7, below the skin, the controlled release is most effective. The complexes will preferably be dispersed in a vehicle to provide a composition having a pH of about 6.5 to about 9 for passage through the skin upon typical administration to provide controlled release of the metal ions upon presentment of endogenous reacting moieties that are associated with inflammatory or arthritic activities.

In accordance with this description and the presently preferred embodiment, it will become apparent that other metal complexes of polyfunctional organic ligands respond to the model of this invention where they exhibit the dissociation property characterized by a sigmoidal curve on a standard pM-pH diagram. For example, based upon the monometal-polyfunctional organic ligand complex of this invention, other metal ions of a monovalent or multivalent nature, specifically, divalent and polyvalent cations including zinc, nickel, chromium, bismuth, mercury, silver, cobalt, and other similar metallic or heavy metal cations may be employed. Other polyfunctional organic ligands may be substituted for the citric acid specifically exemplified by the preferred embodiment of this invention. Included among other polyfunctional ligands are the broader class of alpha or beta hydroxy polycarboxylic acids into which class the citric acid falls. Also, other functionally substituted acids such as alpha or beta amino, sulfhydro, phosphinol, etc., can be substituted in the molecular model of the metal complex of this invention and similar results can be achieved. In general, from a metal complex formula standpoint, the monometal complex of copper and citric acid corresponds to either of the following structural forms (A) and (B).

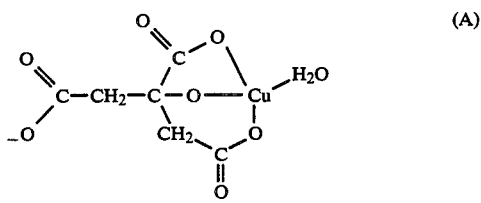

(A)

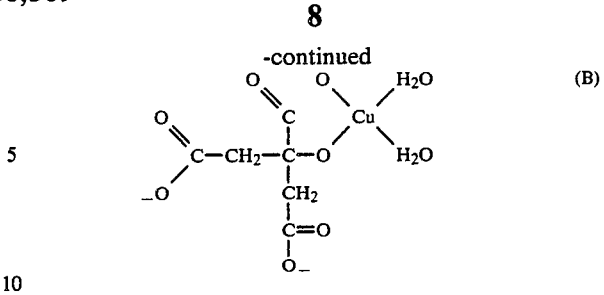

(B)

The (A) form is believed to be the preferred form by applying free energy considerations. A single proton introduced into the complex structure represented by either form (A) or (B) prevents deformation of stable five- or six-member coordinate rings. With the introduction of a proton, only seven-member rings may be formed by the coordination of the acetate electron donors and such seven-member ring structures are unstable. Therefore, the complex molecule dissociates and presents the metal ion for its anti-inflammatory or anti-arthritic effects.

The (A) and (B) structural forms may be more generally represented by the following models:

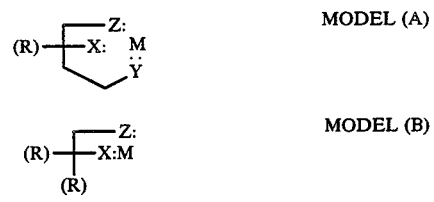

MODEL (A)

MODEL (B)

In the above models, the solid line segments represent a chemical bond between elements in the skeletal structure of the molecules; X, Y and Z represent electron pair donors; (R) represents any elemental or molecular species or group; M represents a metal and wherein the proton affinity of X is greater than that of Z, Y or R. It will therefore be appreciated that other Lewis base proton pairs, and other metal ions, may be substituted into these structural models for oxygen, divalent copper, or, for that matter, the carbon atoms to provide a molecular model which will similarly dissociate upon the introduction of one proton or similarly behaving species as exhibited by the sigmoidal behavior on a pM-pH diagram. The molecular models are thus alternative expressions for the complexes of this invention.

The unusal steric configuration of the molecules of these copper complexes imparts to it a dipolar nature which is characterized by the solvation of water at either pole in a rather rigid, highly polarized manner. This characteristic allows the hydrated complex to electrostatically adsorb to the surfaces of finely divided particles possessing either electronegative or electropositive surface characters. It also permits the "shielded" copper in the complex to migrate intact through membranes such as cell walls of microbes. While no present direct evidence of intact transport has been obtained, all collective results enable one to inductively reason that such transport occurs. $^{64}$Cu-citrate labelling should even quantitate the diffusion of 1:1 metal complexes through skin and cell membranes. The result is that the complex containing the metal ion can travel into areas which otherwise exclude similar compounds. For example, the application of copper salts to a proteinaceous membrane results in the attachment of the copper ions to the membrane components as in the formation of copper proteinates or salts. Little if any of the copper ion, in a soluble, ionized state progresses far beyond the membrane surface. Secondarily, copper salts tend to be corrosive in nature, causing various types of lytic reactions to occur with respect to animal tissue.

Referring to the background of this invention, copper complexes such as copper-amine complexes are known to traverse membranes, but because the copper ion is very tightly bound and/or shielded from the copper acceptor site, the copper ion is essentially unavailable to perform very useful functions, biochemically speaking. In contrast, the unique proton induced dissociation of complexes of this invention renders copper ions to be made readily available as follows:

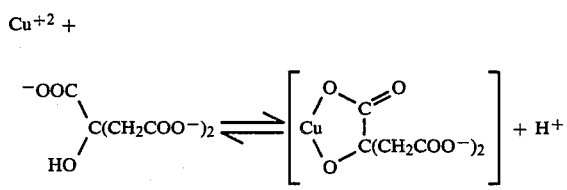

In addition, then, to the dipolar character of the 1:1 copper complex of this invention, it exhibits, most importantly, a relatively weak formation constant ($K_f$) meaning that the copper acceptors with stronger $K_f$ values can remove the copper ion from the 1:1 copper complex. This is accomplished in vivo by such structures as free amino acid groups, sulfhydryl radicals and any Lewis acid which can react with the coordination bonds holding the copper in place. That is, insertion of a hydrogen ion into the system can replace the displaced hydrogen ion originally associated with alcoholic hydroxyl group of the citrate moiety, thereby destabilizing the complex. Hence, the complex is characterized by possessing a proton induced dissociation character. This property is important in the pharmacodynamics of the copper complex of this invention in its use in the treatment of inflammation or arthritis.

In the topical application of the anti-inflammatory agents, it has been found that certain steps should be taken to obtain the desired results. The skin comprises a protective film covering the stratum corneum having a pH of about 4.5 to 6.5 attributed to the presence of free amino acid groups, sulfhydryl groups and other Lewis acids. Below the protective film, the remainder of the skin layers have a more neutral to basic pH of about 7.35 to about 7.45. In one aspect of this invention, anti-inflammatory compositions are buffered so as to neutralize the acidic environment initially encountered in the stratum corneum upon topical application, thereby enabling the copper complexes to pass through the skin for the desired activity below the skin upon demand. This invention thus provides unique compositions having metal complex agents which can traverse the acidic semi-permeable membrane of the skin intact and, once having traversed such membrane, to release ionized copper species at the targeted inflammatory or arthritic sites.

Accordingly, the broadest aspect of my invention is to provide novel and improved anti-inflammatory metal complexes and novel methods of treating inflammation caused by injury, animal cell destruction or disease. More preferably, these metal compositions can be utilized to treat all forms of inflammation in animals including arthritis and more specifically osteoarthritis or rheumatoid arthritis. Further, these novel metal complexes can be utilized to treat inflammation wherein said inflammation is synovitis, gonococcal arthritis, gout, spondylitis, or arthrosis deformans or any combination thereof. The incorporation of the designated forms of inflammation or arthritis provides examples rather than limitations, wherein the methods and novel metal complexes, according to the descriptions and preferred embodiments of this invention, can be employed. Still further, because of the anti-bacterial properties, these novel metal compositions can be utilized to treat infections associated with inflammation.

The method of my invention comprises administering the novel anti-inflammatory metal complexes topically or subcutaneously. The topical method comprises physically applying and perfricating the anti-inflammatory metal complex to the epidermal area of the body affected with inflammation. The subcutaneous method involves introducing the antiinflammatory metal complexes directly below the skin at the targeted site, for example, therapeutic implants or inserts may be used to deliver the metal complexes.

In still another aspect of the present invention, the novel compositions diffuse through the skin and animal cell membranes intact. This is not to say that the metal complexes may not dissociate at all while diffusing through the skin or animal cell membranes. It is believed, however, that the efficiency of the complexes in use is attributed to the design of the metal complexes which maximizes the delivery of the metal ions to the targeted inflammatory or arthritic areas. In other words, a metal ion is transported through the skin and presented to inflammatory or arthritic areas having an endogenous reacting moiety demanding said metal ion wherein said metal ion is released in a controlled manner upon demand. This novel method provides the inflammatory area with greater amounts of metal ion for therapeutic treatment of inflammation. Further, the amount of metal ion released is controlled by the endogenous demanding moiety and pH at the inflammatory site. Still further, the unique properties of these novel metal complexes permit their incorporation into vehicles with an adjusted pH to minimize the amount of metal ions being released prior to reaching the targeted inflammatory area. In substance, these novel metal complexes are uniquely and advantageously designed to dissociate at physiological pH, maximizing the release of metal ions at the inflammatory sites having the desired demanding moieties.

As mentioned above, the novel metal complexes are dispersed in a suitable vehicle to form an embrocation that can be topically applied and perfricated. The main requirement for a suitable vehicle is a stable environment in which the metal complex can be dispersed to formulate a final embrocation that can be topically applied to the epidermis and perfricated. The vehicles can either be aqueous or oleophilic. Because of the dipole characteristic and stability of these metal complexes in aqueous environments, these novel metal complexes can be dispersed in oil and water dispersions. The vehicles that can be used according to the detailed descriptions and preferred embodiments of this invention are ointments and the more preferred forms are creams, gels, water or emulsion-like lotions. Anionic, nonionic and amphoteric emulsifying agents can be used to disperse the metal complexes in the vehicle. It has been found that lotions are not as desirable for topical application as creams which provide a better consistency for perfrication. Further, creams and more specifically greaseless cold creams can be formulated to avoid or minimize the chemical incompatibilities which may otherwise occur between the metal complexes of this invention and the vehicles. Generally, the cold creams to be employed as vehicles in this invention comprise emulsifiers, hydrocarbon waxes, glycols and water. More particularly, the emulsifiers can be anionic, nonionic or amphoteric; the hydrocarbon waxes include petrolatum, wax, paraffin, ceresin, and synthetic polymer waxes, and the polyhydric alcohols or glycol ethers including diethylene glycol, propolyene glycol or glycerol. The emulsifiers are used to disperse the metal complexes in the cream, the hydrocarbon waxes are used as emollients and stiffening agents, while the glycols act as humectants to stabilize the emulsion. A preferred greaseless cold cream vehicle to be used with the metal complexes of this invention consists of glyceryl monostearate, white wax, ceresin, petrolatum (soft), glycerin and water. Typically, a composition of the present invention comprises a metal complex dispersed in an oil-in-water emulsion with an emulsifying agent selected from the group of anionic, nonionic and amphoteric agents by providing in the aqueous phase a dialkali metal monocopper(II) citrate in an amount of about 5% to about 15% w/w and more preferably about 10% w/w in a suitable vehicle at a pH of about 7 to about 9. A preferred anti-inflammatory composition comprises disodiummonocopper(II) citrate in an amount of about 10% w/w in a water-dispersible, greaseless cream base vehicle comprised of an oil-in-water emulsion having a buffered pH of about 7.

The inventor's U.S. Pat. Nos. 4,180,473, 4,129,509 and 4,055,655, disclose methods for the preparation of the 1:1 metal complexes, and methods for the determination of dissociation of such complexes which are suitable for use in the compositions and methods of this invention. Such disclosures are incorporated herein by reference.

The invention, its principles and objectives, and its various embodiments and advantages will be further understood with reference to the following examples and detailed descriptions which illustrate the preparation of the complexes, their activity and their use as anti-inflammatory or anti-arthritic agents.

PREPARATION OF THE METAL COMPLEXES AND ANTI-INFLAMMATORY COMPOSITIONS

The following methods were employed to prepare the compositions of this invention. Generally, the metal complexes were formed by complexing the metal ions with agents possessing reducing capabilities, such as reducing sugars, primary and secondary amines and structures with similar properties, to form complexes or salts. In the following examples, disodiummonocopper(II) citrate (MCC) was employed. This copper citrate complex was made as follows:

Ingredients 65 ml water
61 gms citric acid, anhydrous
35 gms basic copper carbonate [$CuCO_3 \cdot Cu(OH)_2 \cdot H_2O$]
60 gms sodium bicarbonate ($NaHCO_3$)

The citric acid was dissolved in the water. The basic copper carbonate was added with stirring and dispersed well. This mixture was allowed to react for approximately 10 minutes or until the foam ($CO_2$ generation) subsided. Sodium bicarbonate was added slowly with gentle mixing until the pH was between 5.5 and 6.0. The solution was mixed until a black granular precipitate was no longer visible [$Cu(HCO_3)_2$]. The remainder of the sodium bicarbonate was added slowly with gentle stirring to adjust the pH to 7.0 for storage. The soluble copper chelate was thus prepared free from a second salt.

Other techniques for making the complexes are set forth in my U.S. Pat. No. 4,278,610, col. 5, lines 65–68 and col. 6, lines 1–57.

In order to formulate MCC into lotions, creams and the like, it was necessary to be very critical in the choice of ingredients. MCC was found to be chemically incompatible with many substances. As developed above, the compositions of this invention must also provide a pH which will not deleteriously affect the activity of the complex. A unique and advantageous formulation for a skin cream base to be utilized with the metal complexes of this invention was found to satisfy the chemical demands and incompatibility problems of the metal complexes, e.g., MCC, as well as the aesthetic requirements as follows:

| GREASELESS COLD CREAM BASE | |
|---|---|
| Glyceryl monostearate | 11 gms |
| White wax | 2 gms |
| Ceresin | 3 gms |
| Petrolatum, soft | 4 gms |
| Glycerin | 6 gms |
| Water | 74 gms |
| Total | 100 gms |

The fatty acid ester, glyceryl monostearate, acts as an anionic emulsifier in the system to create an emulsion of "oil-in-water" and to disperse the metal complexes, e.g., MCC, into cream. Such an emulsifying agent has been found preferred. The white wax and ceresin acted as stiffening agents. The petrolatum (soft) was an emollient. Glycerin acted as a humectant to stabilize the emulsion. The cream base was made by simply weighing and combining all the ingredients in the order listed into a single container. The mixture, with slight and constant mixing, was brought to boiling, and then stirred until cooled. Violent agitation was avoided to eliminate beating into the cream too much air. If the dispersion was not satisfactory, the ingredients were reheated and then restirred until cooled.

In order to formulate an anti-inflammatory skin cream, powdered (spray-dried) MCC was added to the above skin greaseless cream base. The MCC employed was synthesized according to the above method which yielded a second salt-free product. The product of this synthesis was in an aqueous solution containing approximately 100 mg of copper $Cu^{++}$/ml. The spray-dried MCC was prepared by simple evaporation and, finally, in a Niro® countercurrent 304 stainless steel spray dryer which utilized wheel atomization and single point collection. The product obtained by this process was a finely divided blue powder of uniform particle size which contained approximately 3% moisture. The solid form of MCC was added to the desired percentage of w/w in various vehicles. That is, in order to manufacture a 10% w/w dispersion, a 10 gms portion of MCC spray-dried powder was added to 90 gms of the greaseless cream base prepared from the above-listed ingredients. The greaseless cream base was prepared as stated above. After cooling, a quantity of the base sufficient to make 100 gms was added to a vessel. The MCC powder was added with constant stirring which dissolved it in the water phase of the cream base. The level of active MCC was determined by extraction of the oil phase components employing normal butanol in saturated potassium chloride solution. To a tube containing equal volumes of the above was added a 1 gm aliquot of the MCC-greaseless cream base dispersion. The oil phase components were essentially totally extracted into the butanol while the water soluble constituents, including the MCC, were retained in the aqueous potassium chloride layer. Because of the high concentration of MCC, i.e., 10% w/w, direct spectrophotometric evaluation was performed at once to identify the complex by its absorption maximum of 738 nm., and its concentration was compared by its absorbance readings with those of standard solutions of MCC.

Other cream bases were employed which contained minimal amounts of substances known to react with the 1:1 complex copper, e.g., triethanolamine, disodium EDTA, stearic acid, and the like. If such a base was employed, more of the MCC than that calculated to comprise 10% w/w was incorporated so as to, in effect, satisfy the demand for copper by such endogenous demanding moieties. This approach was workable and has been employed in certain trials because the cream base, although containing certain relatively chemically incompatible substances, offered, for instance, improved texture, more pleasing coloration, and, was generally more available on a commercial scale than the above-described, essentially totally compatible, greaseless cream base formula.

Water Base

A simple MCC aqueous solution was prepared by dissolving a sufficient amount of powdered (spray-dried) MCC into distilled water, referred to hereinafter as "MCC liquid."

Lotion Base

A lotion formulation was prepared by introducing in a sufficient quantity powdered (spray-dried) MCC into a lotion vehicle comprising water, glycerin, mineral oil, stearic acid, glycol stearate and other ingredients, triethanolamine, acetylated lanolin alcohol, glyceryl stearate, acetyl alcohol, fragrance, dimethicone, magnesium aluminum silicate, methylparaben, propylene glycol, propylparaben, carbomer-934, disodium EDTA, D & C Red No. 19, D & C Yellow No. 10 and more commonly known as Vaseline Brand Intensive Care lotion. Again, as stated above, this lotion contained small amounts of EDTA which chelated, preferentially, some of the copper. Thus, a slight excess (less than 1% w/w) of powdered (spray-dried) MCC was added to correct this deficiency.

The above cream and lotion bases are adjusted to about 7 by employment of common acid, e.g., HCl, or base, e.g., NaOH. The systems are also buffered with sodium borate-boric acid and sodium carbonate-bicarbonate. Several types of the above preparations of this invention were retained for several years and exhibited satisfactory stabilities. Buffered creams or liquids prepared according to the above procedures, or similar procedures, were employed in the following examples.

Anti-Inflammatory and Anti-Arthritic Activity

The following are examples of a series of confirmed cases of osteoarthritis and rheumatoid arthritis treated with the topical metal complex disclosed by this invention. Generally, the medication was composed of the active ingredient, disodiummonocopper(II) citrate (MCC), C.A.S. Registry Number: 65330-59-8, dispersed in various vehicles including water, gels, creams and emulsion-type lotions. All of the cases incorporated herewith, as examples, were confirmed diagnostically by physicians employing the usual examining techniques, i.e., physical examination, radiography, etc. The ages of the patients who participated in these examples ranged from 38 years to 83 years. The average duration of illness in this population was 11 years, ranging from 3 to 25 years.

All of the patients in these examples, prior to their treatment with the metal complexes of this invention, had received standard courses of therapy including applications of heat; exercise; salicylates to tolerance; indomethacin; oral and intraarticular steroids. One of the patients had undergone total hip replacement prior to treatment. At least one of the patients had been treated previously with intravenous gold preparations and cytoxan. All of the patients had, through the course of the disease, grown progressively worse with reference to articular swelling and disturbances in articular mobility. Deformities, particularly in the interphalangeal articulations, continued to progress. A common, subjective symptom was arthralgia in all cases.

Upon instituting topical therapy with the copper complexes as disclosed herein, the patients were restricted from using any other medication including aspirin. Most patients had been using nothing but aspirin upon institution of the therapy, having given up on the usual remedies. Specific excerpts from each patient history are disclosed in the following examples. The topical anti-inflammatory or anti-arthritic embrocations employed in these examples were MCC liquids and/or MCC greaseless cold creams.

EXAMPLE I

MCP, PIP, DIP and CMC are used hereinafter to define metacarpophalangeal joints, proximal interphalangeal joints, distal interphalangeal joints and carpometacarpal joint, respectively.

A 38 year old, male caucasian, Market Researcher, suffered from rheumatoid arthritis for a duration of 3 years. His symptoms were: pauciarticular, bilateral MCP's, no apparent systemic involvement.

Following treatment, flaring subsided within two weeks; increased range of motion with no pain by the third week; simultaneously, visible, measurable reduction in edema. After one month of daily application to the affected areas, treatment was stopped. Approximately three weeks later, flaring became evident. Treatment was begun again; flaring did not recur. The patient applied the medication once per week to the affected area and, both subjectively and objectively, was essentially asymptomatic. No adverse side effects of any kind were noted during treatment with these copper complexes. This patient relied heavily on typing as a part of his livelihood and was able to resume meaningful, productive activity.

Duration of treatment was 25 months. Dosage form: MCC Liquid, 10%; MCC Greaseless Cold Cream, 5%, 10%.

EXAMPLE II

An 83 year old, female caucasian, housewife, suffered from osteoarthritis for 25 years. Her symptoms were pauciarticular, bilateral PIPs, DIPs.

Following treatment, pain diminished within one week; while motion was possible prior to treatment, it was extremely painful. After two weeks of treatment, tenting of the hands, which had been secondary to attempts to alleviate pain, was reduced so that the palmar surface of the hand was brought into approximately parallel contact with a flat surface. This patient complained of skin irritation at the sites of application. Examination of the patient revealed an extremely thin, onionskin-like stratum corneum. The concentration of the active ingredient was reduced approximately 10-fold; and the medication was applied at the same daily interval according to regimen. The irritation persisted and some pain was said to be felt to return. The original strength preparation was then employed at every-other-day intervals. The irritation subsided. The pain did not return. This patient was able to knit and crochet and perform various household tasks such as lifting and had, essentially, a vastly expanded range of motion compared to her pretreatment status. The patient continued to use the preparation on an every-other-day basis without experiencing any adverse side affects.

Duration of treatment was 23 months. Dosage form: MCC Greaseless Cold Cream, 1%, 10%.

EXAMPLE III

A 68 year old, male caucasian, tool and die maker, suffered from osteoarthritis for 10 years. His symptoms were pauciarticular, bilateral CMCs, PIPs.

The patient complained of extreme sensitivity to tactile stimuli and limited ability to grip tightly. Patient experienced flares on a weekly basis for approximately 10 years. Slight deformity in the PIPs of the index fingers was noted. Following treatment, flaring subsided within three weeks; the ability to grip tightly with no attendant pain was noted after three weeks. Following one month of daily application, the CMC and PIP edema was objectively reduced. Treatment of the right hand was stopped at this time; treatment of the left hand continued. After approximately three weeks, tenderness in the CMC and PIP of the index finger of the right hand returned; minimal flaring occurred according to the patient. A placebo preparation was applied to both hands, with cessation of treatment with active ingredient of the left hand also. Within two weeks, the patient complained of a return of the inability to grip tightly, stating that it was painful once again. The placebo was replaced with the active preparation and, within two days, the symptoms decreased. Within one week, the patient was asymptomatic. The patient has applied the product daily and has had no adverse side effects of any kind. This patient was required to exercise great manual dexterity in the performance of his job. He was able to return to work as a tool maker following treatment.

Duration of treatment was 22 months. Dosage form: MCC Greaseless Cold Cream, 0%, 1%, 2%, 5%, 10%.

EXAMPLE IV

A 66 year old, male caucasian, master machinist, suffered from osteoarthritis for 7 years. His symptoms were pauciarticular, bilateral MCPs, PIPs, DIPs, and Right CMC.

This case is very similar to Example III, above. The third week of treatment was accompanied by a restored mobility in all affected joints with no attendant pain. His grip was strong and sure. He has continued to apply the medication daily and has had no sequellae. This patient had taken early retirement from his career as a master machinist due to his inability to hold tools; following one month of therapy, he returned on a part-time basis and has continued to work effectively with no arthritic manifestations.

Duration of treatment was 21 months. Dosage form: MCC Liquid, 5%, 10%; MCC Greaseless Cold Cream 5%, 10%.

EXAMPLE V

A 65 year old, male caucasian, industrial engineer, suffered from osteoarthritis of the right knee for 9 years.

The medication was topically applied around the patellar margin on a twice-daily basis which resulted in a marked reduction of pain after ten days. The patient walked with a limp prior to treatment; two months after treatment was initiated, the patient walked with a normal gait. The patient continued to apply the medication on a daily basis and no adverse side effects were noted. The patient states that he was able to dress himself whereas he had required aid prior to treatment because of the stiff, painful knee condition.

Duration of treatment was 6 months. Dosage form: MCC Greaseless Cold Cream, 10%..

EXAMPLE VI

A 60 year old, female caucasian, housewife, suffered from osteoarthritis for 3 years. Her symptoms were limited to the PIP and DIP of her right index finger.

Treatment was applied twice a day; after one week, patient stated that the pain was much less intense. Patient stated that she had no real limitation in motion but that the pain was constant and annoying but not unbearable. Three weeks of treatment resulted in the complete cessation of pain which did not return.

Duration of treatment was 6 months. Dosage form: MCC Greaseless Cold Cream, 10%.

EXAMPLE VII

A 79 year old, male caucasian, retired banker, suffered from osteoarthritis for 9 years of the right shoulder. He had extremely limited range of motion without pain and was unable to lift his arm above his head without severe pain.

The medication was applied to the humeroclavicular joint area on a twice-daily basis. The pain subsided within two weeks and the patient was able to put on his hat with his right hand for the first time in about six years. Patient did continue to apply the preparation with no adverse side effects.

Duration of treatment was 13 months. Dosage form: MCC Greaseless Cold Cream, 10%.

EXAMPLE VIII

A 52 year old, male caucasian, physician, suffered from rheumatoid arthritis for four years. His symptoms were pauciarticular of both hands and both wrists. His right hand manifestations were more pronounced and the area most severely affected was the MCP joint.

His range of motion was somewhat impaired and the pain was dull and constant. The application of the preparation resulted in an immediate tingling sensation in the area of application which persisted on a constant basis.

He also reported having a metallic taste in his mouth about one hour following the application. The metallic taste, however, seemed to last for only a few minutes. The pain ceased approximately two weeks following initiation of treatment which consisted of twice-a-day application to the affected joints. The patient found that he had more freedom of motion of the more seriously affected MCP joints stating that he did not realize that he had been that "impaired." This patient stopped using the preparation and the MCP pain returned within one month. He reinstituted the therapy and continued to be asymptomatic with no adverse side effects.

Duration of treatment was 10 months. Dosage form: MCC Greaseless Cold Cream, 10%.

EXAMPLE IX

A 68 year old, male caucasian, dry cleaner/tailor, suffered from osteoarthritis for 16 years. His symptoms consisted of fusion of PIPs and MCPs on his left hand. Further, there was severe impairment of motion and complete inability to grasp objects with his right hand because of the apparent fusion of PIP and MCP on his right index finger.

Patient stated that he was unable to lift 5-gallon containers of cleaning fluid due to intense pain upon application of force to right hand. Patient applied the medication twice a day to the painful but not totally immobile PIP and DIP joints of the right hand. After one month, the pain had disappeared, as had edema which was palpable prior to the treatment. An approximate 4 mm decrease in the circumferential measurement of the involved PIP joints of the right hand indicated a definite recession of the inflammatory process. Patient stated that he is now able to lift heavy objects with no pain and was able to operate certain machinery in his business which he was unable to do for at least 10 years.

Duration of treatment was 10 months. Dosage form: MCC Greaseless Cold Cream, 10%.

EXAMPLE X

A 72 year old, male caucasian, retired military officer, suffered from osteoarthritis for 10 years had monoarticular involvement in the right knee and was unable to walk without the aid of a cane.

His leg was stiff, due to incipient tetany secondary to self-imposed restriction of flexion in his attempt to minimize the pain. Radiographs indicated a severe inflammatory process with slight erosion of the femoral epiphysis. Spur formation, however, was not visualized. Medication was applied around the patellar margin on a twice-daily basis. In two weeks, the patient was able to flex the knee approximately 45° with no pain. After six weeks of application, the patient was able to both rotate and flex the knee in a full range. The patient continued to apply the medication on a twice-daily basis with no adverse side effects.

The patient was able to walk without a cane and was able to ambulate freely. He was involved in a course of physical therapy in an attempt to restore his muscle tone. He walked with a slight limp, probably due to the degenerative process noted above.

Duration of treatment was 11 months. Dosage form: MCC Greaseless Cold Cream, 10%.

EXAMPLE XI

A 62 year old, male caucasian, retired steel mill worker, suffered from osteoarthritis of the right hip joint for 20 years.

His left hip had been surgically replaced with a complete prosthesis due to severe necrosis of the femoral articulation surfaces. Pain and lack of motion with minimal degeneration of the acetabulum and the femoral head had caused this patient to consider a second prosthesis. The medication was applied twice daily to the entire hip region from the iliac crest in a triangular fashion to approximately 5 cm below the articulation. After approximately one month, the pain upon motion was greatly reduced. After approximately six weeks, the pain was alleviated. A relatively full range of motion was restored to a point matching that of the prosthesis of the other hip. Radiography indicated no further degenerative change.

It would appear that surgical intervention was obviated in this patient. The patient continued to function in a normal fashion and used the medication once a day.

Duration of treatment was 19 months. Dosage form: MCC Greaseless Cold Cream, 10%.

EXAMPLE XII

A 75 year old, female caucasian, retired clerk typist, suffered from osteoarthritis for 19 years. She had bilateral involvement of all DIPs, PIPs and MCPs with gross deformity but minimal fusion.

This patient had telescoping of the PIP of the left index finger. Her motion was severely limited and her ability to grasp objects was essentially absent. She had to be waited on by family members. After two weeks of therapy, which consisted of twice-a-day application of the medication, pain in all affected joints was markedly reduced. In the third week of treatment, range of motion of all joints except those of the right index finger was restored to approximately 50% level. One month following inception of treatment brought essentially complete relief from pain. Patient was referred to physical therapy and had approximately 75% restoration of function of both hands.

Dosage form: MCC Greaseless Cold Cream, 10%.

In view of the above detailed descriptions and preferred embodiments, it will be apparent that other modifications of these inventions may be made without departing from the spirit and scope thereof.

What is claimed is:

1. A method of alleviating an inflammatory disorder in an animal which comprises delivering to the site of the inflammation of said disorder an effective anti-inflammatory amount of a metal complex consisting of dialkali metal monoheavymetal chelate of an alpha or beta-hydroxy polycarboxylic acid.

2. The method of claim 1 wherein said metal complex is topically administered to the skin of the body portion afflicted with said disorder.

3. The method of claim 2 wherein said metal complex is dispersed in a vehicle to provide a composition having a pH above about 7.

4. The method of claim 2 wherein said metal complex diffuses through the skin intact to facilitate subcutaneous release of said metal ion.

5. The method of claim 1 wherein said metal complex is introduced subcutaneously at the location of said disorder.

6. The method of claim 1 wherein said complex is dispersed in a vehicle to provide a composition having a pH of about 6.5 to about 9.

7. The method of claim 1 wherein said complex is dialkalimetal monocopper (II) citrate.

8. The method of claim 7 wherein said complex is in aqueous admixture.

9. The method of claim 8 wherein the admixture has a pH of about 7 to about 9.

10. The method of claim 1 wherein said metal ion is copper.

11. The method of claim 1 wherein said disorder is a tissue response to injury or destruction of animal cells.

12. The method of claim 11 wherein said disorder is arthritis.

13. The method of claim 12 wherein said arthritis is osteoarthritis or rheumatoid arthritis.

14. The method of claim 11 wherein said disorder is arthralgia.

15. The method of claim 11 wherein said disorder is microbially infected.

16. The method of claim 11 wherein said disorder is synovitis, gonococcal arthritis, gout, spondylitis, or arthrosis deformans or any combination thereof.

17. The method of claim 8 wherein said admixture is an oil and water dispersion.

18. The method of claim 8 wherein said admixture further contains a vehicle for said complex.

19. The method of claim 18 wherein said vehicle comprises an emulsifier, a hydrocarbon wax, a polyhydric alcohol and water.

20. The method of claim 19 wherein said vehicle is a cream base comprising in an amount of about 11% w/w glyceryl monostearate, about 2% w/w white wax, about 3% w/w ceresin, about 4% w/w petrolatum, about 6% w/w glycerin, and about 74% w/w water.

21. The method of claim 8 wherein said admixture is oleophilic.

22. The method of claim 8 wherein said complex is disodium monocopper(II) citrate.

23. An anti-inflammatory composition containing as the active anti-inflammatory ingredient a monometal complex consisting of dialkali metal monoheavymetal chelate of an alpha or beta-hydroxy polycarboxylic acid and an acceptable vehicle wherein said composition has a pH which will not deleteriously dissociate said complex.

24. The composition of claim 23 wherein said composition has a pH in excess of about 7.

25. The composition of claim 23 wherein said complex is dispersed in a vehicle having a pH within the physiological range of about 7 to about 9.

26. The composition of claim 25 wherein said complex is dialkalimetal monocopper (II) citrate.

27. The composition of claim 26 wherein said complex is in aqueous admixture.

28. The composition of claim 27 wherein the pH range of the composition is from about 7 to about 9.

29. The composition of claim 23 wherein said metal ion is copper.

30. The composition of claim 27 wherein said admixture is an oil and water dispersion.

31. The composition of claim 27 wherein said admixture further contains a vehicle for said complex.

32. The composition of claim 31 wherein said vehicle comprises an emulsifier, a hydrocarbon wax, polyhydric alcohol and water.

33. The composition of claim 32 wherein said vehicle is a cream base comprising glyceryl monostearate as the emulsifier.

34. The composition of claim 32 wherein said vehicle comprises glyceryl monostearate, white wax, ceresin, petrolatum, glycerin and water.

35. The composition of claim 27 wherein said admixture is oleophilic.

36. The composition of claim 23 wherein said metal complex is contained in a dispersion of oil and water with an emulsifier agent selected from the group of anionic and nonanionic agents by providing in the aqueous phase a dialkalimetal monocopper(II) citrate in an effective anti-inflammatory amount at a pH of about 7 to about 9.

37. The composition of claim 36 wherein said dialkalimetal monocopper(II) citrate is about 5% to about 15% w/w of said composition.

38. The composition of claim 36 wherein said composition comprises disodium monocopper(II) citrate in an amount of about 10% w/w in a water-dispersable cream base vehicle comprising an oil-in-water emulsion having a pH of about 7.0.

* * * * *